United States Patent
Nasu et al.

(10) Patent No.: US 11,298,589 B2
(45) Date of Patent: Apr. 12, 2022

(54) FOOT TRAINING DEVICE AND FOOT TRAINING METHOD

(71) Applicant: NASYU CO., LTD., Owariasahi (JP)

(72) Inventors: Tomokazu Nasu, Owariasahi (JP); Keiichi Sakai, Owariasahi (JP); Naoji Sakai, Owariasahi (JP)

(73) Assignee: NASYU CO., LTD., Owariasahi (JP)

( * ) Notice: Subject to any disclaimer, the term of this patent is extended or adjusted under 35 U.S.C. 154(b) by 0 days.

(21) Appl. No.: 17/048,229

(22) PCT Filed: Mar. 4, 2020

(86) PCT No.: PCT/JP2020/009070
§ 371 (c)(1),
(2) Date: Oct. 16, 2020

(87) PCT Pub. No.: WO2020/217722
PCT Pub. Date: Oct. 29, 2020

(65) Prior Publication Data
US 2021/0236879 A1    Aug. 5, 2021

(30) Foreign Application Priority Data
Apr. 24, 2019   (JP) .............................. JP2019-082666

(51) Int. Cl.
*A63B 23/10* (2006.01)
*A63B 21/02* (2006.01)

(52) U.S. Cl.
CPC ............ *A63B 23/10* (2013.01); *A63B 21/028* (2013.01)

(58) Field of Classification Search
CPC ................. A63B 23/10; A63B 21/028; A63B 6/00–02; A63B 21/0004–00043;
(Continued)

(56) References Cited

U.S. PATENT DOCUMENTS

| 4,461,472 A | * | 7/1984 | Martinez ................ | A63B 23/10 482/128 |
| 5,180,171 A | * | 1/1993 | Panzica .................. | A63B 65/00 473/569 |

(Continued)

FOREIGN PATENT DOCUMENTS

| CN | 204815545 U | 12/2015 |
| JP | S54-154634 A | 12/1979 |

(Continued)

OTHER PUBLICATIONS

Lighthouse Document (derived from: Lighthouse Christian Products, "Lighthouse Christian Products All Things Through Christ Fire Red 5 Inch Foam Rubber Squeezable Palm Cross" [online], Dec. 21, 2015 [retrieved on Sep. 29, 2021], Amazon, Retrieved from: https://www.amazon.com/Lighthouse-Christian-Products-Things-Squeezable/dp/B00BI20766?th=1) (Year: 2015).*

(Continued)

*Primary Examiner* — Joshua Lee
*Assistant Examiner* — Catrina A Letterman
(74) *Attorney, Agent, or Firm* — Oliff PLC (57) ABSTRACT

A training device is provided for training a foot using the device. The training device includes a fulcrum placed at a center and four projections that project in different directions from the fulcrum. Each of the four projections have elastic members that are bendable. The training device is configured to improve foot muscle strength by bending and stretching the elastic members. At least two of the four projections have different degrees of elasticity in flexure as determined when a force is applied to a distal end of each of the at least two projections to bend the elastic members. The four projections project in cross directions from the fulcrum at the center. Each pair of projections that oppose each other across the fulcrum are arranged on a straight line.

6 Claims, 6 Drawing Sheets

(58) Field of Classification Search
CPC ........ A63B 21/00178; A63B 21/00189; A63B 21/045–0552; A63B 21/0607; A63B 21/0615; A63B 21/40; A63B 21/4015; A63B 21/4019; A63B 21/4023; A63B 21/4034–4035; A63B 2022/0094; A63B 2023/006; A63B 23/08; A63B 23/14; A63B 23/16; A63B 26/003; A63B 2208/0204–0209; A63B 21/00061; A63B 21/00058; A63B 21/025; A63B 21/0455; A61H 2001/027; A61H 1/0266; A61F 5/019; A63H 33/065
USPC ........................................................ 446/486
See application file for complete search history.

(56) References Cited

U.S. PATENT DOCUMENTS

| | | | | |
|---|---|---|---|---|
| D340,480 S | * | 10/1993 | Cummings | D21/437 |
| 5,681,243 A | * | 10/1997 | Criss | A63B 21/028 |
| | | | | 482/49 |
| 5,743,831 A | * | 4/1998 | Jakich | A63B 23/0458 |
| | | | | 482/34 |
| 5,830,109 A | * | 11/1998 | Juarez | A63B 23/16 |
| | | | | 482/44 |
| D686,374 S | * | 7/2013 | Nazimek | D30/160 |
| 2009/0156367 A1 | * | 6/2009 | Harris, Jr. | A63B 21/055 |
| | | | | 482/49 |
| 2014/0066269 A1 | * | 3/2014 | Wheler | A63B 21/0607 |
| | | | | 482/110 |
| 2019/0070459 A1 | * | 3/2019 | Michaud | A63B 21/00047 |

FOREIGN PATENT DOCUMENTS

| | | |
|---|---|---|
| JP | S55-62357 U | 4/1980 |
| JP | 2011-212420 A | 10/2011 |
| JP | 2012-148038 A | 8/2012 |
| JP | 2016-150211 A | 8/2016 |

OTHER PUBLICATIONS

Feb. 22, 2021 Office Action issued in Chinese Patent Application No. 202080002692.7.

Aug. 9, 2021 Office Action issued in Chinese Patent Application No. 202080002692.7.

* cited by examiner

FOOT TRAINING DEVICE AND FOOT TRAINING METHOD

TECHNICAL FIELD

The present invention relates to a foot training device and a foot training method, and more particularly relates to a foot training device including an elastic member that can be bent using foot muscles and a method for training a foot using the device.

BACKGROUND ART

Conventionally, training devices, such as the one disclosed in Patent Literature 1, including in a portion thereof a rod-shaped elastic member such as a coil spring have been used for strength training of the arms and the like. Such training devices are used to build up muscle strength by bending and stretching the elastic member under a load applied by the elastic force of the elastic member.

In a training device such as the one disclosed in Patent Literature 1, if it is desired to change the magnitude of the training load, for example, the elastic member can be replaced with another elastic member having a different flexural modulus. However, since a heavy weight is applied to the training device during use, the training device needs to have a structure that is strong enough to resist the heavy weight, and, in many cases, the structure does not allow for replacement of elastic members of the training device. Even if replacement is possible, it is necessary to prepare a plurality of elastic members, and therefore, it is not easy to change the magnitude of the load.

In contrast, Patent Literature 2 discloses a training device in which a friction member is employed, and the load can be easily changed by changing the pressing strength of the friction member. However, the training device disclosed in Patent Literature 2 has a complex structure compared with the training device disclosed in Patent Literature 1.

Moreover, although various training devices for improving the muscle strength of the arms, legs, trunk, and the like are known including those disclosed in Patent Literature 1 and Patent Literature 2, training devices for improving the muscle strength of the feet including a sole are not much used. However, in view of improving the ability to move the entire body and maintaining health for elderly people, and the like, the importance of strengthening foot muscles has been gaining particular attention in recent years.

CITATION LIST

Patent Literature

PTL 1: JP 2012-148038 A
PTL 2: JP S54-154634 A

SUMMARY OF INVENTION

Technical Problem

The present invention was made in view of the above-described problems, and it is an object thereof to provide a foot training device having a simple structure and making it possible to easily change the magnitude of the load, and a method for training a foot using the training device.

Solution to Problem

To address the above-described problems, a foot training device according to the present invention includes a fulcrum placed at a center, the four projections projecting in different directions from the fulcrum, each of the four projections having, at least in a portion thereof, an elastic member that is bendable in a bending direction, wherein the training device is configured to be used to improve foot muscle strength by bending and stretching the elastic member, at least two of the four projections have different degrees of elasticity in flexure as determined when a force is applied to a distal end of each of the at least two projections to bend the elastic member; the four projections project in cross directions from the fulcrum at the center, and, for each pair of projections that oppose each other across the fulcrum, the projections are arranged on a straight line; and none of the four projections has an annular structure.

It is preferable that each elastic member is a plate-shaped or rod-shaped member made of a resin material or a rubber material.

It is preferable that at least two of the four projections have different lengths. It is particularly preferable that all of the four projections have different lengths.

Preferably, each elastic member is a plate-shaped or rod-shaped member made of a resin material or a rubber material, and the elastic members constituting at least two of the four projections have different flexural moduli or cross-sectional areas.

It is preferable that the projections have a length of 5 to 20 cm.

It is preferable that the foot training device includes an elastic body layer and two protective layers that are stacked together, the elastic body layer being made of a plate-shaped resin material or rubber material, and the two protective layers being made of a resin material or a rubber material having a lower elastic modulus than the elastic body layer and a higher foaming ratio than the elastic body layer, and being provided on two plate surfaces of the elastic body layer, respectively.

A first foot training method according to the present invention includes the steps of: placing the above-described foot training device according to the present invention on a floor surface, bringing a heel of a foot into contact with the foot training device, hooking a toe around an end edge of the distal end of at least one of the projections, pulling up the distal end of the projection in this state, and bending and stretching the projection using muscles of a sole, thereby improving muscle strength of a sole.

A second foot training method according to the present invention includes the steps of: holding one of the projections of the above-described foot training device according to the present invention between two adjacent toes of a foot, bringing a heel of the foot into contact with the training device, pulling up the projection in this state, and bending and stretching the projection using muscles of a sole, thereby improving muscle strength of a sole.

Advantageous Effects of Invention

According to the present invention, it is possible to provide a foot training device having a simple structure and making it possible to easily change the magnitude of the load.

The foot training device according to the present invention includes the fulcrum placed at a center, the four projections projecting from the fulcrum, each of the four projections having, at least in a portion thereof, an elastic member that is bendable in the bending direction. At least two of the four projections have different degrees of elasticity in flexure as determined when a force is applied to the distal end of each of the at least two projections to bend the elastic member. Thus, the magnitude of the load can be easily changed by selecting the projection to be used during training.

"Degree of elasticity in flexure" means the bendability of a projection when it is bent. The higher the degree of elasticity in flexure, the harder it is to bend the projection, and the higher the training load. In the case where each elastic member is formed of a plate-shaped or rod-shaped member made of a resin material or a rubber material, the degree of elasticity in flexure of an elastic member is increased by increasing the flexural modulus or the cross-sectional area of the constituent material, and is increased by reducing the length of the constituent material. The degree of elasticity in flexure of a projection is increased by increasing the degree of elasticity in flexure of the elastic member forming the projection, and is also increased by reducing the overall length of the projection. That is to say, the degree of elasticity in flexure of the projections can be varied by adopting a configuration in which the projections have different lengths or a configuration in which the elastic members constituting the projections have different flexural moduli or different cross-sectional areas. With the configuration in which the projections have different lengths, it is easy to vary the degree of elasticity in flexure of the projections. On the other hand, with the configuration in which the elastic members constituting the projections have different flexural moduli or different cross-sectional areas, it is easy to greatly vary the degree of elasticity in flexure of the projections, and excellent variety of load is thus obtained. Note that the flexural modulus of an elastic member means a value obtained from the amount of displacement (strain) that occurs in the elastic member when it is bent and the amount of force applied.

Varying the length of the projections means the following: it is sufficient that the overall length of the projections from the fulcrum to the respective distal end is varied, and the length of the elastic members constituting the projections may be varied, or the length of portions other than the elastic members may be varied. When the overall length of projections is varied, due to leverage, for example, in the case where the elastic member of a longer projection is bent and stretched by holding the distal end of the projection, the elastic member can be bent and stretched with a smaller amount of force than in the case where the elastic member of a shorter projection is bent and stretched by holding the distal end of the projection. That is to say, a longer projection has a lower degree of elasticity in flexure, and accordingly a lower training load, than a shorter projection. Also, a longer elastic member itself constituting a projection has a lower degree of elasticity in flexure, and accordingly a lower training load.

In particular, with regard to the structure of the training device including the four projections, a training device in which the four projections project in cross directions from the fulcrum at the center, and, for each pair of projections that oppose each other across the fulcrum, the projections are arranged on a straight line is suitable for foot training. In particular, a configuration in which all of the four projections have different lengths makes it possible to select at least four different levels of load and is therefore particularly preferable.

The training device according to the present invention is suitably used as a foot training device for improving the muscle strength of a sole by bending and stretching a projection using muscles of a sole. As a specific example of the method for improving the muscle strength of a sole, a method is conceivable, as described above as the foot training method according to the present invention, the method including the steps of: placing the training device on a floor surface or the like, bringing a heel of a foot into contact with the training device, hooking a toe around an end edge of the distal end of at least one of the projections, pulling up the distal end of the projection in this state, and bending and stretching the projection using muscles of a sole. Moreover, another training method is also conceivable, the other method including the steps of: holding one of the projections of the foot training device between two adjacent toes of a foot, bringing a heel of the foot into contact with the training device, pulling up the projection in this state, and bending and stretching the projection using muscles of a sole. It is possible to effectively strengthening the muscles of a sole, mainly a transverse arch portion and a medial longitudinal arch portion, by performing these training methods.

The foot training device according to the present invention makes it possible to select the training load and select a variety of methods of use, and is therefore suitable as a training device for strengthening muscles of a sole using a variety of methods and a variety of loads. Since none of the projections of the training device is provided with an annular structure into which a toe can be inserted, it is possible to prompt a user, during training, to bend and stretch a projection by hooking a toe around the end edge of the distal end of the projection, or by holding the projection between toes. As a result, a load is effectively applied to muscles of a sole, especially muscles of the arch portions, and a high training efficiency can thus be obtained.

It is particularly preferable for the foot training device that the lengths from the fulcrum to the distal ends of the respective projections are within a range of 5 to 20 cm.

When the foot training device includes an elastic body layer and two protective layers that are stacked together, the elastic body layer being made of a plate-shaped resin material or rubber material, and the two protective layers being made of a resin material or a rubber material having a lower elastic modulus than the elastic body layer and a higher foaming ratio than the elastic body layer, and being provided on two plate surfaces of the elastic body layer, respectively, a foot comes into contact with the training device via the protective layers, and an excellent texture is thus obtained during use. The foot training device achieves both a good training effect provided by the elastic body layer and an improvement of the texture provided by the protective layers.

DESCRIPTION OF EMBODIMENTS

Structure of Foot Training Device

Figure 1:
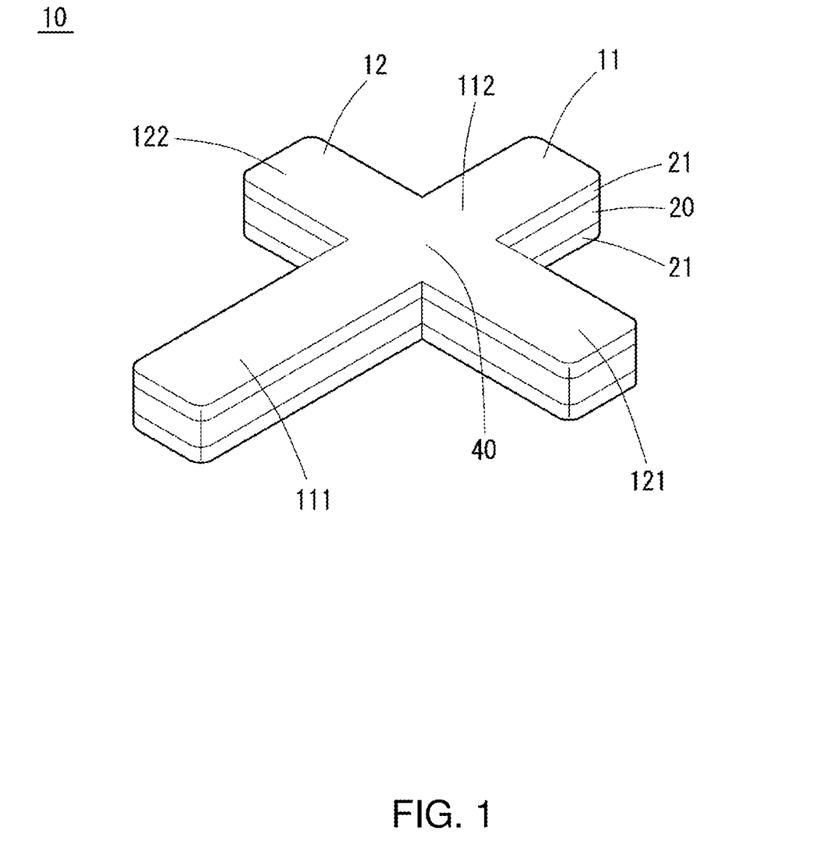
FIG. 1 is a perspective view showing the external appearance of a foot training device according to an embodiment of the present invention.
Figure 2:
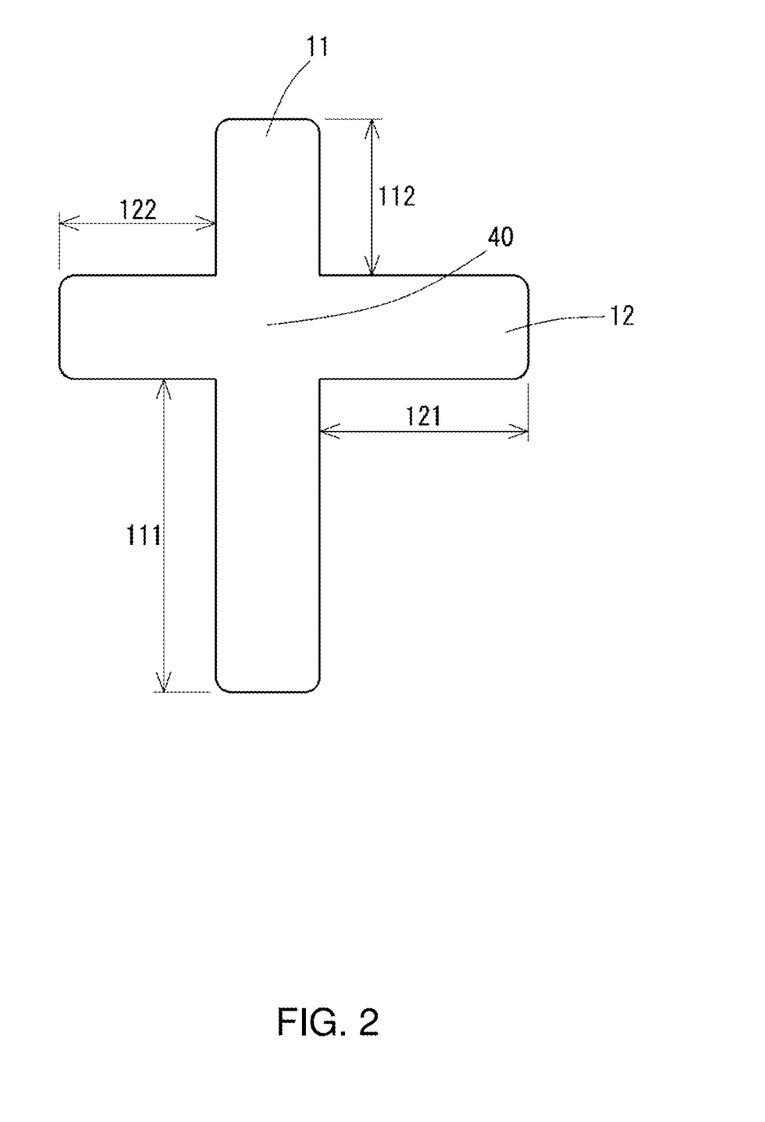
FIG. 2 is a top view of the foot training device in FIG. 1.

A foot training device according to an embodiment of the present invention will be described in detail with reference to the drawings. FIG. 1 is a perspective view showing the external appearance of a foot training device according to an embodiment of the present invention, and FIG. 2 is a top view of the foot training device. The foot training device (hereinafter also referred to simply as the "training device") according to the present embodiment is used for the purpose of training a foot.

A training device 10 includes an elastic body layer 20 formed of elastic members that are bendable in a bending direction, the elastic body layer being shaped to have projections with different lengths, namely, a first projection 111, a second projection 112, a third projection 121, and a fourth projection 122, that project in cross directions in the same plane from a fulcrum 40 at the center. The first projection 111 and the second projection 112 are arranged on a straight line on opposite sides of the fulcrum 40, and the third projection 121 and the fourth projection 122 are arranged on a straight line on opposite sides of the fulcrum 40. A straight-line portion including the first projection 111 and the second projection 112 is referred to as a first straight-line portion 11, and a straight-line portion including the third projection 121 and the fourth projection 122 is referred to as a second straight-line portion 12. The fulcrum 40 is a portion where the first straight-line portion 11 and the second straight-line portion 12 intersect, and is less bendable than the other portions of the projections, or is unbendable, because the two straight-line portions intersect. The training device 10 can be used to improve muscle strength by bending and stretching the projections formed of the elastic members.

The entire elastic body layer 20 is formed of the elastic members that are bendable in the bending direction. For the elastic members that are bendable in the bending direction, it is preferable to use a resin material, such as a styrene resin, an olefin resin, a vinyl chloride resin, a vinyl acetate resin, a urethane resin, an amide resin, or an elastomer other than these; a rubber material, such as natural rubber, a diene synthetic rubber, or a non-diene synthetic rubber; or the like. The resin material or the rubber material may be used in the form of a foam. When the material is used in the form of a foam, it is easy to adjust the training load to a desired magnitude by varying the foaming ratio.

The training device 10 may also have a protective material with cushioning properties on a portion or the entirety of an outer peripheral surface of the elastic body layer 20. In the present embodiment, protective materials 21 are provided on upper and lower surfaces of the elastic body layer 20, which constitutes the main body. Preferably, the protective materials 21 are formed of elastic members having a lower elastic modulus than the elastic body layer 20, and, for example, a resin material or a rubber material similar to those of the elastic body layer 20 but having a higher foaming ratio may be used. When the training device 10 has the protective materials 21, the training device 10 provides an excellent texture when it is held. With a configuration of the foot training device 10 in which the elastic body layer 20 is combined with layers of the protective materials 21, both a good training effect and an excellent texture can be achieved by the elastic body layer 20 with the higher elastic modulus having the function of providing a good training effect, and the layers of the protective materials 21 having the function of improving the surface texture.

In the training device 10, the entire projections are formed of the elastic members, and the projections have different lengths. That is to say, the lengths of the elastic members constituting the projections are different, and the lengths of the entire projections are different. Thus, the elastic member of a longer projection has a lower degree of elasticity in flexure than that of a shorter projection, the longer projection is easier to bend by leverage, and the longer projection therefore applies a lower training load. It is possible to select the training load, and easily change the magnitude of the load, by using the projections with different lengths for different purposes.

Moreover, since the entire projections are formed of the elastic members, during use, it is also possible to use the training device 10 by applying a force to a portion of a projection other than a distal end thereof by holding that portion, for example. In this case, if a force is applied to a position that is near the fulcrum, the training load is high, and if a force is applied to a position that is far from the fulcrum, the training load is low.

It is preferable that all of the first projection 111, the second projection 112, the third projection 121, and the fourth projection 122 have different lengths. It is preferable that, when the first projection 111 and the second projection 112, and the third projection 121 and the fourth projection 122, which are arranged on the respective straight lines, satisfy $L_{111} > L_{112}$ and $L_{121} > L_{122}$, where $L_{111}$ is the length of the first projection 111, $L_{112}$ is the length of the second projection 112, $L_{121}$ is the length of the third projection 121, and $L_{122}$ is the length of the fourth projection 122, the ratios $L_{111} : L_{112}$ and $L_{121} : L_{122}$ of the projections arranged on the straight lines are each 3:1 to 3:2. That is to say, it is preferable that the straight line-shaped first straight-line portion 11 and second straight-line portion 12 intersect with each other at a position that is not the center of these straight-line portions in the length direction, or more specifically, at a position where the first straight-line portion 11 and the second straight-line portion 12 are individually divided into two portions in the length direction with a length ratio of 3:1 to 3:2. When the lengths of the projections satisfy this relationship, the first projection 111 and the second projection 112, and the third projection 121 and the fourth projection 122, can be sufficiently varied in terms of the magnitude of the load, using the differences in length therebetween, while the balance of the entire training device is not significantly disturbed. Moreover, when the lengths of the projections are within the above-described range, the variety of load is excellent, and a particularly preferable foot training device is thus obtained.

It is preferable that the length $L_{11}$ of the first straight-line portion 11 and the length $L_{12}$ of the second straight-line portion 12 satisfy the relationship $L_{11} > L_{12}$, and it is preferable that the ratio $L_{11}/L_{12}$ between the lengths is 1.25 to 1.50. When the lengths of the first straight-line portion 11 and the second straight-line portion 12 are within this range, the magnitude of the load can be sufficiently varied using the difference in length between the two straight-line portions, while the balance of the entire training device is not significantly disturbed. Moreover, when the lengths of the straight-line portions are within the above-described range, the variety of load is excellent, and a particularly preferable foot training device is thus obtained.

It is preferable that the lengths of the first projection 111, the second projection 112, the third projection 121, and the fourth projection 122 from the fulcrum 40 to the distal ends of the respective projections are within a range of 5 to 20 cm.

When the lengths of the projections are within this range, a foot training device that is easy to use is obtained.

In the training device 10 according to the present embodiment, the projections 111, 112, 121, and 122 do not have an annular structure into which a toe can be inserted. Examples of annular structures into which a toe can be inserted include a hole formed in the material (elastic member) constituting a projection, and a rubber band or a string attached to a projection. In the form shown in FIG. 1, each of the projections 111, 112, 121, and 122 is configured as a plate-shaped member or a rod-shaped member linearly projecting outward from the fulcrum 40 and having a constant width and thickness, and does not have an annular structure.

Foot Training Method

Next, a method for training a foot using the training device 10 according to the embodiment of the present invention will be described.

Figure 3:
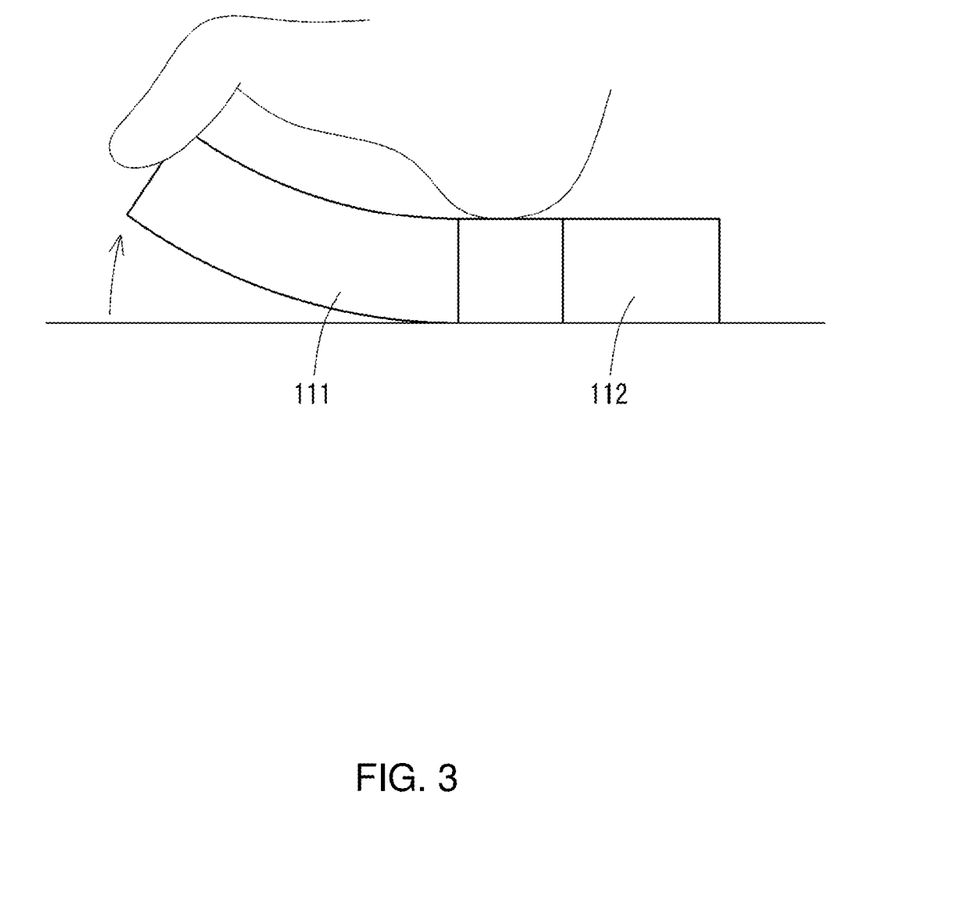
FIG. 3 is a conceptual diagram showing a form in which the foot training device is used.

As shown in FIG. 3, training with the training device 10 can be performed by placing the main body on a floor surface or the like, holding the distal end of one of the projections, and bending and stretching the projection in an upward direction around the fulcrum 40. Specifically, training can be performed by bringing a heel of a foot into contact with a portion near the fulcrum 40, hooking a toe around an end edge of the distal end of the projection, and, in this state, bending a sole so as to pull up a distal end portion of the projection. The exercise of holding the distal end of the projection with a toe and pulling up the projection can strengthen the muscles of a sole, and is particularly effective in training of the transverse arch and a nearby portion of the foot. The training device 10 according to the present embodiment is particularly suitable when used in the above-described manner. Moreover, similar training can also be performed by holding the distal end of one projection with a toe and bringing a heel into contact with another projection opposing the one projection.

In this case, due to leverage, the longer the length to the distal end of the projection, the smaller the force that is required to bend and stretch the projection, and, accordingly, the lower the training load. On the other hand, when the distal end of a projection with a short length to the distal end is held and then bent and stretched, a high load is applied, and, accordingly, a greater training effect is obtained. That is to say, if the lengths from the fulcrum 40 to the respective distal ends have the relationship $L_{111}>L_{121}>L_{112}>L_{122}$, the training effects to be obtained have the following relationship: the fourth projection 122>the second projection 112>the third projection 121>the first projection 111. The projection used can be appropriately selected depending on a desired magnitude of the load, the type of training, and the foot size, and an excellent foot training device is thus obtained.

Figure 4A:
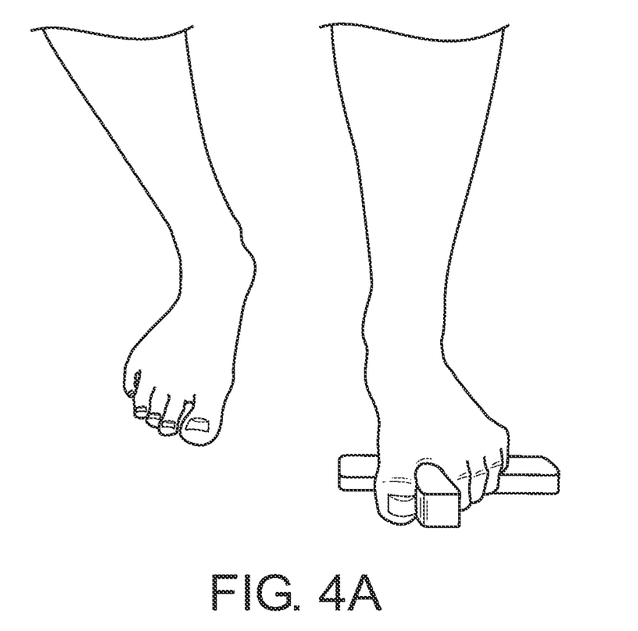
FIG. 4 shows photographs showing other forms in which the foot training device is used.
Figure 4B:
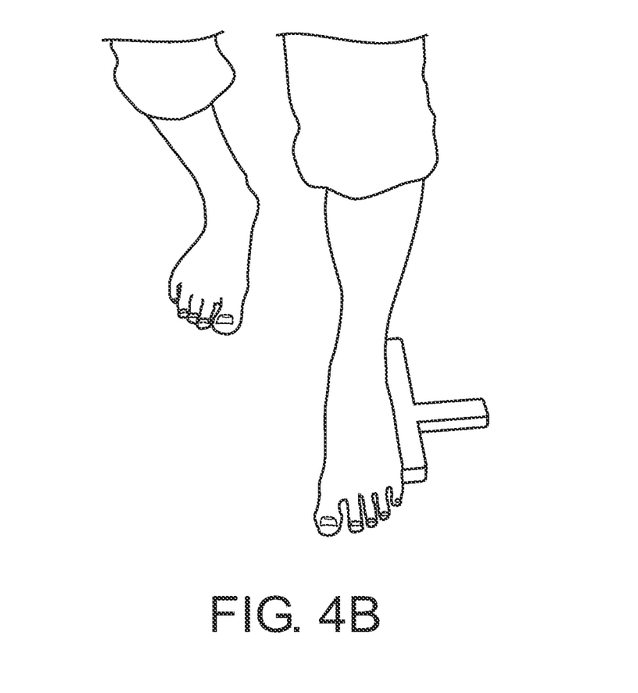

FIG. 4 shows other methods of use for training a foot using the training device 10 according to the present embodiment. For example, the training device 10 may also be used by (a) holding one of the projections between two adjacent toes, for example, between the first and the second toes, of a foot. In this case, it is preferable to hold a portion near the fulcrum 40. The use of the training device 10 in this manner can correct the bones of a foot and strengthen the muscles of a sole, and is particularly effective in training of the medial longitudinal arch and a nearby portion. Furthermore, in this state, the muscles of the entire sole can be strengthened by using the training device 10 by bringing a heel of the foot into contact with the training device 10 and then bending the projection held so as to pull up the projection. Also, muscles of the hip joint that work together with the muscles of a sole can be strengthened simultaneously, by performing an exercise in such a manner that, in the state in which the training device 10 is held between the toes, the training device 10 is lifted from the floor surface using muscles of the thigh. The training device 10 may also be used by (b) pressing a sole against one of the projections and applying body weight thereto. Since the training device 10 has the elastic members that can provide a sufficient training effect, the training device 10 is prevented from excessive deformation when a sole is pressed against the projection, and a sole can thus be sufficiently stimulated. Specifically, this method of use makes it possible to correct the position of the cuboid located in a rear portion of the lateral longitudinal arch by bringing the projection into contact with the position of the cuboid, and consequently activate the muscles of the entire sole. With the above-described methods of use as well, the training device 10 according to the present embodiment makes it possible to appropriately select the projection to be used from the projections with different lengths, and is therefore suitable for a variety of methods of use for activating a foot.

The training device has no annular structure into which a toe can be inserted in any of the projections. Thus, during the training of pulling up a projection, a user is induced to keep the projection by hooking a toe around the end edge of the distal end of the projection as shown in FIG. 3, or by holding the projection between two toes as shown in FIG. 4(a). In the case where a motion of pulling up the projection is performed while maintaining the state in which a toe is hooked on the end edge of the projection and bent or the projection is held between the two toes as described above, the pulling-up cannot be easily achieved, and, furthermore, a high load is applied to the muscles of a sole including a transverse arch portion and a medial longitudinal arch portion. As a result, muscles including the muscles of the arch portions can be effectively strengthened. If a foot training device has an annular structure in a projection, and the projection is pulled up in a state in which a toe is inserted in the annular structure, the projection can be easily pulled up using muscles of the toe itself and muscles of the instep of a foot, by utilizing the engagement of the toe with the annular structure. Thus, the projection can be pulled up with ease without using the muscles of the arch portions of a sole, and it is therefore not possible to effectively strengthen the muscles of a sole including the arch portions.

Training Device According to Variation

Figure 5:
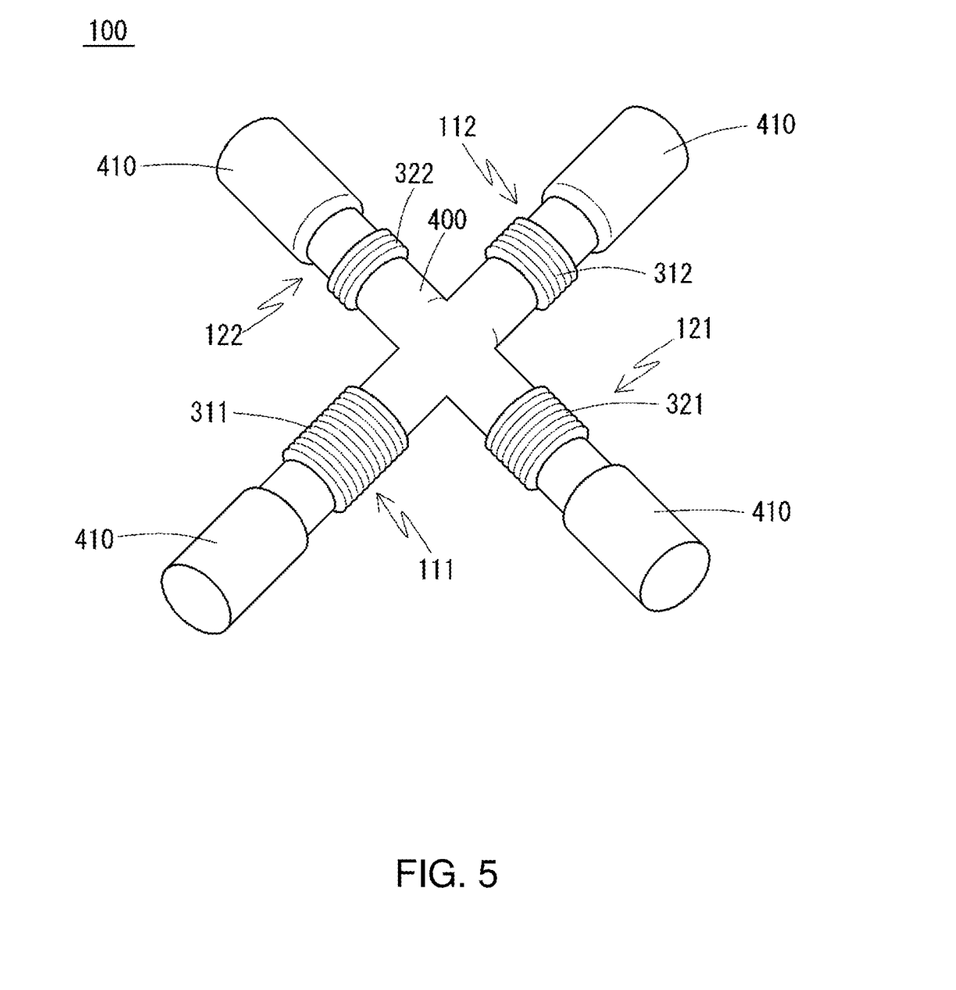
FIG. 5 is a per view showing the external appearance of a training device according to a variation.
Figure 6A:
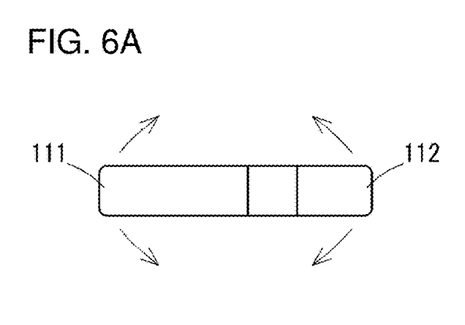
FIG. 6 shows conceptual diagrams showing forms in which the training device according to the variation is used.
Figure 6B:
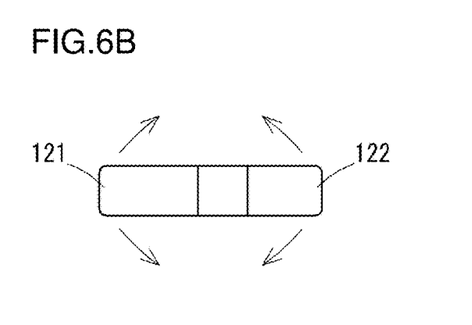
Figure 6C:
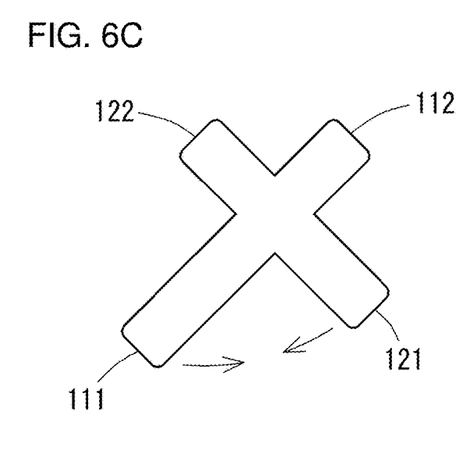
Figure 6D:
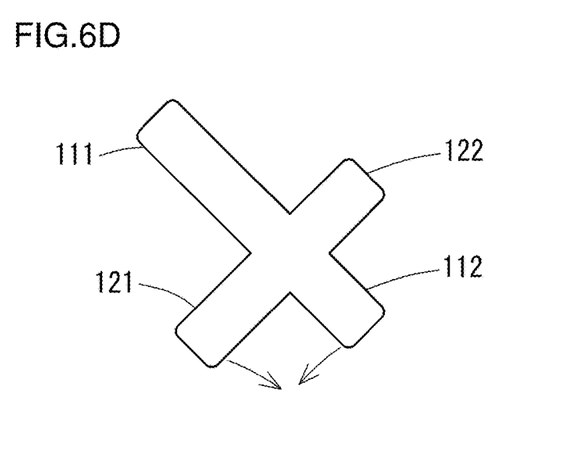
Figure 6E:
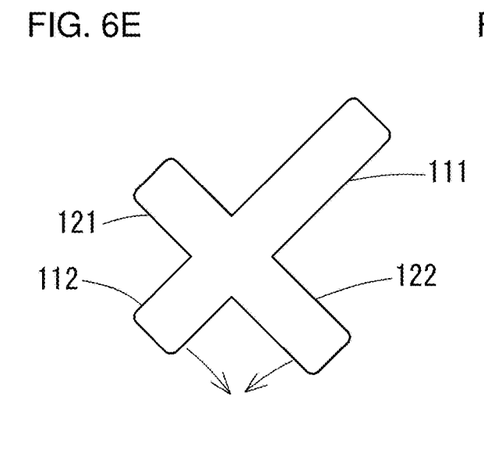
Figure 6F:
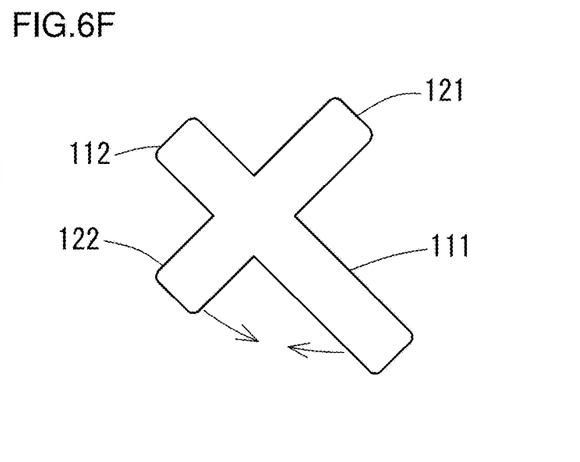

Next, a training device according to a variation will be described. The above-described foot training device 10 has a configuration in which the fulcrum and the projections are integrally formed using a plate-shaped elastic material, and the entire projections are formed of the elastic members, whereas in the variation described here, the fulcrum and the projections are formed separately and then joined together, and the projections each have an elastic member in a portion thereof. The above-described foot training device 10 is suitable for training of a sole, which is a body part with relatively weak muscle strength, whereas the training device according to the present variation is suitable for training of a body part, such as the arms, with relatively strong muscle strength. The form of the training device, the material of the elastic members, the overall size, and the like can be appropriately selected depending on the part to be strengthened.

FIG. 5 is a perspective view showing the external appearance of a training device 100 according to the variation. The training device 100 has a central connecting portion 400, which serves as a fulcrum, at the center, and coil springs, which serve as elastic members, with different lengths are connected to the central connecting portion 400 and thereby form the first projection 111, the second projection 112, the third projection 121, and the fourth projection 122. The first projection 111 and the second projection 112 are arranged on a straight line on opposite sides of the central connecting portion 400, and the third projection 121 and the fourth projection 122 are arranged on a straight line on opposite sides of the central connecting portion 400. These projections form the first straight-line portion 11 and the second straight-line portion 12 as in the foot training device 10 according to the above-described embodiment. A grip 410, which serves as a protective material, is formed on the distal end of each coil spring via a metal pipe. Thus, during use, the training device can be used by holding the grips 410.

The central connecting portion 400 is a metal member obtained by combining cylindrical pipes into a cross shape, and the coil springs are joined to the ends of the four pipes. Connecting portions between the central connecting portion 400 and the individual coil springs are subjected to a high load during use. For this reason, it is preferable that the coil springs are strongly joined to the central connecting portion 400 to such an extent that the connecting portions can resist the load.

With regard to the coil springs joined to the central connecting portion 400, a first coil spring 311 forms the first projection 111, a second coil spring 312 forms the second projection 112, a third coil spring 321 forms the third projection 121, and a fourth coil spring 322 forms the fourth projection 122.

The first projection 111, the second projection 112, the third projection 121, and the fourth projection 122 have different lengths. It is sufficient that the overall lengths of the projections from the fulcrum to the respective distal ends differ from one another, and a configuration may be adopted in which the length of the coil springs constituting the respective projections is varied, or a configuration may be adopted in which the length of portions of the projections other than the elastic members, for example, the length of the metal pipes located between the coil springs and the grips 410 is varied. When the overall length of the projections is varied, due to leverage, the bendability, that is, the elasticity in flexure of the projections also varies in accordance with the lengths of the projections. When the length of the coil springs is varied, the bendability, that is, the elasticity in flexure of the coil springs themselves also varies, and excellent variety of training load is thus obtained.

FIG. 6 shows methods of use of the training device 100 according to the present variation. Note that, in FIG. 6, detailed information about the central connecting portion 400, the coil springs, and the like of the training device 100 is omitted, and only the concept of the projections projecting in the cross directions is schematically shown. As the method of use of the training device 100, for example, the following methods may be used: (a) holding the two ends of the first straight-line portion 11, that is, the distal end of the first projection 111 and the distal end of the second projection 112 and bending and stretching the training device 10 such that the two distal ends are brought closer to each other; and (b) holding the two ends of the second straight-line portion 12, that is, the distal end of the third projection 121 and the distal end of the fourth projection 122 and bending and stretching the training device 10 such that the two distal ends are brought closer to each other. In this case, the shorter the length between the two ends, the higher the load, and, regarding the training effect, a relationship b>a holds. Note that, in the case where the foot training device 10 according to the above-described embodiment is used in a manner such as those shown in FIG. 3 or 4(a), even when the training device is used by holding one projection with a toe and bringing a heel into contact with the projection opposing the one projection, as described above, the training load is high if the straight-line portion with the shorter overall length is used. The training device 100 may also be used by holding projections that are not directly opposite each other. Specifically, the training device 100 may also be used by holding (c) the distal end of the first projection 111 and the distal end of the third projection 121, (d) the distal end of the second projection 112 and the distal end of the third projection 121, (e) the distal end of the second projection 112 and the distal end of the fourth projection 122, or (f) the distal end of the first projection 111 and the distal end of the fourth projection 122, and bending and stretching the training device such that the two distal ends are brought closer to each other. When the relationship between the lengths from the central connecting portion 400 to the respective distal ends is $L_{111} > L_{121} > L_{112} > L_{122}$, the magnitude of the load decrease in the order of e>d>f>c.

The training device 100 according to the present variation is suitably used by holding a grip(s) 410 with hand, and is suitable for performing training for building up the muscle strength of body parts, such as the arms, the chest, and the back, that are capable of applying a stronger force than the feet, by holding two of the grips 410 and bending and stretching the training device 100 in the bending direction as described above. In this case, the lengths of the projections can be set to 15 to 60 cm.

Other Forms

In the foregoing description, a form in which the degree of elasticity in flexure is varied by varying the length of the projections has been described using the foot training device 10 and the training device 100 according to the variation. Alternatively, the degree of elasticity in flexure of projections of a training device may be varied by varying the flexural modulus or the cross-sectional area of elastic members constituting the projections. The higher the flexural modulus of the elastic member constituting a projection, the higher the degree of elasticity in flexure of the elastic member. Also, the larger the cross-sectional area of the elastic member, the higher the degree of elasticity in flexure of the elastic member. Specific examples of such a training device include a training device having a structure in which, as is the case with the foot training device 10 shown in FIG. 1, the length, in the width direction or the thickness direction, of projections constituted by integrally formed elastic members is varied; and a training device having a form in which, as is the case with the training device 100 shown in FIG. 5, a plurality of elastic members are connected to a fulcrum, and having a structure in which coil springs with different flexural moduli are used as the coil springs connected to the central connecting portion 400; and the like. In these cases, the projections may have the same length or different lengths. When the projections have the same length, the degree of elasticity in flexure can be varied by varying only the flexural modulus or the cross-sectional area of the elastic members, and a desired training load is thus likely to be obtained. With a configuration in which the degree of elasticity in flexure of the projections is varied by varying the flexural modulus or the cross-sectional area of the elastic members constituting the projections, the degree of elasticity in flexure of the projections is likely to be varied greatly, and excellent variety of load is thus obtained.

Moreover, in the foregoing description, training devices having four projections with different degrees of elasticity in flexure have been described as the foot training device 10 and the training device 100 according to the variation. However, there is no particular limitation on the number of projections, and it is sufficient that the training device has at least two projections with different flexural moduli. In the case where a training device includes only two projections, it is preferable that the two projections are not arranged on a straight line, from the viewpoint of the ease of forming the fulcrum, for example.

Although embodiments of the present invention have been described above, the present invention is not limited to the above-described embodiments and examples, and various modifications may be made thereto without departing from the gist of the present invention.

The invention claimed is:

1. A foot training device comprising:
a fulcrum placed at a center; and
four projections projecting in different directions from the fulcrum, each of the four projections having, at least in a portion of each of the four projections, an elastic member that is bendable in a bending direction, wherein:
the training device is configured to be used to improve foot muscle strength by bending and stretching one or more of the elastic members, and at least two of the four projections have different degrees of elasticity in flexure as determined when a force is applied to a distal end of each of the at least two projections to bend the elastic member,
the four projections project in cross directions from the fulcrum at the center, and, for each pair of projections that oppose each other across the fulcrum, the projections are arranged on a straight line,
none of the four projections has an annular structure, and
all of the four projections have different lengths.

2. A foot training method comprising the steps of:
placing the foot training device according to claim 1 on a floor surface;
bringing a heel of a foot into contact with the foot training device;
hooking a toe around an end edge of the distal end of at least one of the projections;
pulling up the distal end of the projection in this state; and
bending and stretching the projection using muscles of a sole, thereby improving muscle strength of the sole.

3. A foot training method comprising the steps of:
holding one of the projections of the foot training device according to claim 1 between two adjacent toes of a foot;
bringing a heel of the foot into contact with the training device;
pulling up the projection in this state; and
bending and stretching the projection using muscles of a sole, thereby improving muscle strength of the sole.

4. A foot training device comprising:
a fulcrum placed at a center;
four projections projecting in different directions from the fulcrum, each of the four projections having, at least in a portion thereof, an elastic member that is bendable in a bending direction; and
an elastic body layer and two protective layers that are stacked together, the elastic body layer being made of a plate-shaped resin material or rubber material, the two protective layers being made of a resin material or a rubber material having a lower elastic modulus than the elastic body layer and a higher foaming ratio than the elastic body layer, and the two protective layers being provided on two plate surfaces of the elastic member, respectively, wherein:
the training device is configured to be used to improve foot muscle strength by bending and stretching one or more of the elastic members, at least two of the four projections have different degrees of elasticity in flexure as determined when a force is applied to a distal end of each of the at least two projections to bend the elastic member,
the four projections project in cross directions from the fulcrum at the center, and, for each pair of projections that oppose each other across the fulcrum, the projections are arranged on a straight line, and
none of the four projections has an annular structure.

5. A foot training method comprising the steps of:
placing the foot training device according to claim 4 on a floor surface;
bringing a heel of a foot into contact with the foot training device;
hooking a toe around an end edge of the distal end of at least one of the projections;
pulling up the distal end of the projection in this state; and
bending and stretching the projection using muscles of a sole, thereby improving muscle strength of the sole.

6. A foot training method comprising the steps of:
holding one of the projections of the foot training device according to claim 4 between two adjacent toes of a foot;
bringing a heel of the foot into contact with the training device;
pulling up the projection in this state; and
bending and stretching the projection using muscles of a sole, thereby improving muscle strength of the sole.

* * * * *